(12) United States Patent
Wire et al.

(10) Patent No.: US 6,524,563 B1
(45) Date of Patent: Feb. 25, 2003

(54) HAIR TREATMENT COMPOSITIONS

(75) Inventors: Stephen Lee Wire, Wirral (GB); Keith Leslie Rutherford, Wirral (GB); Robert George Riley, Wirral (GB); David Howard Birtwistle, Edgewater, NJ (US)

(73) Assignee: Unilever Home & Personal Care, USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/696,444

(22) Filed: Oct. 25, 2000

(30) Foreign Application Priority Data

Oct. 27, 1999 (GB) .............................................. 9925439

(51) Int. Cl.[7] .......................... A61K 7/06; A61K 7/075; A61K 7/08; A61K 7/00; A61K 6/00
(52) U.S. Cl. ................ 424/70.12; 424/70.1; 424/70.19; 424/401; 424/47; 424/70.21; 424/70.24; 424/70.27; 424/70.28
(58) Field of Search ............................ 424/70.1, 70.11, 424/47, 724, 600, 70.27, 70.12, 70.19, 70.21, 70.24, 70.28, 401; 510/119

(56) References Cited

U.S. PATENT DOCUMENTS

| | | | |
|---|---|---|---|
| 4,000,317 A | 12/1976 | Menda et al. | |
| 4,351,754 A | * 9/1982 | Dupre | ........................ 524/445 |
| 4,482,850 A | 11/1984 | Sonoda et al. | |
| 4,940,578 A | 7/1990 | Yoshihara et al. | |
| 5,500,223 A | * 3/1996 | Behan et al. | ................. 424/451 |
| 5,501,727 A | * 3/1996 | Wang et al. | ................... 106/35 |
| 5,507,965 A | * 4/1996 | Padoy et al. | ................ 252/62.2 |
| 5,520,908 A | 5/1996 | Lundmark | |
| 5,599,531 A | * 2/1997 | Holcomb | |
| 5,607,667 A | * 3/1997 | Holcomb | |
| 5,658,573 A | 8/1997 | Holcomb | |
| 5,833,967 A | 11/1998 | Ramin | |

FOREIGN PATENT DOCUMENTS

| | | |
|---|---|---|
| DE | 38 36 907 A1 | 5/1990 |
| EP | 0313307 | 4/1989 |
| EP | 0478326 | 4/1992 |
| EP | 0 855 178 A2 | 7/1998 |
| JP | 7 215 828 | 7/1995 |

OTHER PUBLICATIONS

Search Report under Section 17 Application No. GB 9925439.3 dated Feb. 11, 2000.

* cited by examiner

*Primary Examiner*—Thurman K. Page
*Assistant Examiner*—Humera N. Sheikh
(74) *Attorney, Agent, or Firm*—Matthew Boxer

(57) ABSTRACT

A hair treatment composition which comprises 0.01–5.0 wt % of a particulate substance which is substantially unagglomerated or unaggregated prior to incorporation in the composition, which particulate substance has a modal primary particle size of 7–40 nm, and a Youngs modulus of at least 4 Gpa, preferably at least 6 GPa.

23 Claims, 1 Drawing Sheet

WET AND DRY PEAK COMBING FORCES FOR CONDITIONERS A, B, AND C. ERROR BARS 95% CONFIDENCE LIMITS.

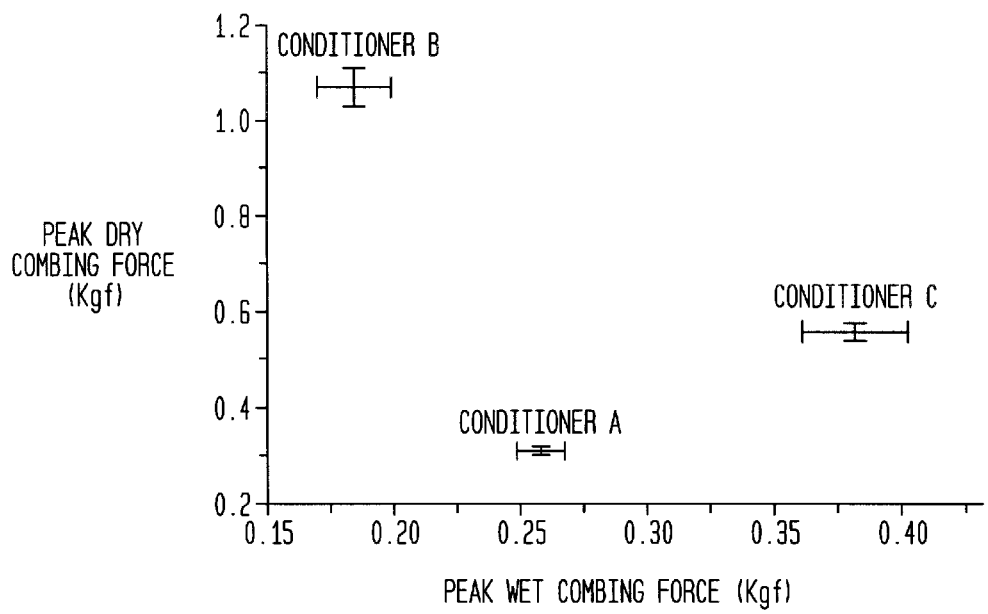

HAIR TREATMENT COMPOSITIONS

The invention relates to hair treatment compositions, which may be of the "wash off" or "leave on" variety, containing specified particulates which enhance the in- and post-use properties of the composition.

It is generally desirable to be able to deliver from a hair treatment composition the property of causing individual hairs to be able to retain a configuration relative to each other. In the context of wash off compositions (such as shampoos or conditioners), if the composition is appropriately delivered and the hair is appropriately dried, this may take the form of causing the hair to develop body. In many instances this may be considered desirable, especially if the hair is initially fine. The development of body may have aesthetic benefits, as well as causing the hair to be relatively easy to subsequently style.

If the benefit is delivered from a so called leave on composition, such as a gel, mousse, cream, lotion, spray, or air infused styling foam (which products utilise propellant free pumps), the benefit may take the form of providing the hair with styling benefits, and in particular allowing the hair to retain a given style for a longer period of time.

We have surprisingly found that it is possible to incorporate certain specific small particulate solids into hair treatment compositions, which have been found to provide benefits in relation to prevention of hair strands moving relative to each other. In the context of wash off compositions such as shampoos or conditioners, the solids may provide the composition with the capacity to bodify treated hair which is appropriately styled, without adversely affecting the wet conditioning characteristics. In this context the word "style" is given its usual meaning in the art, which is the act of creating a style in the hair, often after some initial drying. In any event the act of styling usually requires that the hair retains a given configuration, with individual hair shafts generally retaining their configuration relative to each other.

In the context of leave on products, the solids may allow a left on styling composition to retain a given style on treated hair.

The specific solid compounds which allow the hair treatment compositions to have these properties are small, initially unagglomerated, unaggregated particles typically of modal particle size 7–40 nm, and which are relatively hard. As such, they typically have a Youngs modulus of more than about 4, preferably more than about 5, more preferably greater than about 6 GPa, more preferably greater than about 10 GPa. A preferred category of compounds typically has a Youngs modulus of about 20–100 Gpa, preferably 40–90 Gpa, even more preferably 50–90 GPa. Suitable solids for use according to the invention include certain specific silicas.

The incorporation of small particulates into hair treatment compositions is known. A number of patent publications describe the use of silicas in hair treatment compositions. Many of these are compositions describe some form of aggregated or agglomerated silicas, which are commonly referred to as silica gel, hydrated silicas, fumed silicas or precipitated silicas.

Hereinafter we refer to terminology commonly used in art, namely that aggregates are understood to be secondary particles which are a collection of primary particles which have fused to form face to face sintered structures, which cannot be dissociated, and as such are relatively hard. Agglomerates are understood to be tertiary particles, which are networks of aggregates which are loosely connected at discreet points.

Representative of the art in this area is U.S. Pat. No. 5,520,908 (Minnetonka Research Institute), which describes the use of hydrated silica in cosmetic compositions such as hair treatment compositions, which may provide benefits such as enhanced shine and feel. It is well known that in the manufacture of such hydrated silicas, the silica is subject to a treatment step (usually heating) which involves the joining of the primary silica particles to each other by covalent bonding.

Other types of fine particulates are known for use in hair treatment compositions, to provide a variety of benefits. For example, EP-A-855,178 (Kao) describes hair care products containing silicone elastomer powders which are said to have a particle size in the region of 0.01–100 microns, for the purpose of improving the softness, smoothness and long lasting conditioning of the hair. Such particles are however relatively soft and elastic.

Oil absorptive polymers which have a relatively small particle size are known from U.S. Pat. No. 4,940,578 (Kao). These are said to have a particle size in the region of 0.005–30 microns, but again the particles employed are relatively soft and elastic.

A number of publications also refer to the use of "colloidal silica" in hair treatment compositions, but it is clear from the source of e colloidal silica employed that the silica referred to is actually substantially aggregated or agglomerated. Representative of such publications are U.S. Pat. No. 5,833,967 (L'Oreal), JP 7215828 (Kao), and DE 3836907 (Wella).

In these documents, it is found that primary particle sizes are referred to which are of the order of a few nanometers. However, the actual silicas which are referred to and utilised in the examples which are commercially available are materials such as Cab-O-Sil (trade mark) and Aerosil (trade mark) silicas. Referring to the suppliers literature on such silicas, it is clear that whilst these materials have primary particle sizes in the ranges quoted, the materials themselves are actually substantially aggregated or agglomerated, so as to provide large populations of secondary or tertiary particles which in fact typically have dimensions which are of the order of hundreds of nanometers, or even microns.

Other patent applications refer to the use of silicas as filler materials for rigid silicone polymers, which themselves may be used as hair styling and conditioning products. Representative of this are U.S. Pat. No. 4,482,850 (Procter & Gamble) and EP-A-313,307 (Procter & Gamble). However in both these instances the silica is intimately bound in a silicone matrix, and again the choice of exemplified silicas indicates that the silicas utilised are themselves aggregated or agglomerated to a substantial degree, prior to inclusion in the compositions.

Silicas are also know as encapsulation materials, which may be incorporated in hair treatment compositions, and representative of this is EP-A-478,326 (Quest). Some of the commercially available silicas utilised as starting materials in this teaching are unaggregated or unagglomerated colloidal materials, such as Ludox HS-40 and Ludox SM. However it is clear that in the process of encapsulating the hydrophobic materials (e.g. perfumes) according to the teaching of this application, once the Pickering emulsion is formed with the silica at the interface between the aqueous and hydrophobic phases, that the silicas are subsequently subjected to a gelling step in which they are hardened around the encapsulated material.

Finally, U.S. Pat. No. 5,658,573 (Holcomb) refers to the use of colloidal silica particles which are said to have a particle size of 1–10 nm, and be charged, in hair treatment compositions for the purpose of enhancing penetration of the hair shaft. However according to this teaching such materials are used at levels of at most 50 ppm, which equates roughly to a usage level of a maximum of 0.005% in topical products.

We have found that the inclusion of a certain levels of a relatively hard, small particulate having a primary particle size in the region of 7–40 nm and being substantially unaggregated or unagglomerated in the pure or unprocessed form leads to beneficial properties in a hair treatment composition. When incorporated into the topical treatment composition, a degree of association between particles may occur, but the associated particles are not thought to be aggregated as such, because of the lack of substantial levels of covalent bonding.

When the treatment composition is a wash off composition such as a shampoo or conditioner composition, the benefit from incorporation of the small particles manifests itself as being an increase in body of the washed or conditioned hair, especially if a subsequent styling regime is followed. When the treatment composition is a leave on composition, it is possible to provide styling benefits.

Such compositions which provide a styling benefit can do so in the absence (or substantial absence) of a styling polymer, which leads to compositions which have a styling benefit, but nevertheless do not suffer from the sensory negatives (primarily stickiness) which are associated with prior styling compositions which are based on a styling polymer.

Thus, according to a first aspect of the invention, there is provided a hair treatment composition which comprises 0.01–5.0% by weight of a particulate substance which is substantially unagglomerated or unaggregated prior to incorporation in the treatment composition, which particulate substance has a modal primary particle size of 7–40 nm, and a Youngs modulus of at least 4 GPa, preferably more than about 5 GPa, preferably greater than about 6 GPa.

In a number of the embodiments, the primary particulates substance may form loose associations aggregates in the topical composition.

According to a further aspect of the invention, there is provided a method of treating hair comprising applying thereto a hair treatment composition which comprises 0.01–5.0% by weight of a particulate substance which is substantially unagglomerated or unaggregated, which has a modal primary particle size of 7–40 nm, and a Youngs modulus of at least 4 GPa, preferably greater than about 6 GPa, and subsequently styling the hair.

According to the method, the treatment composition may be a wash off composition or a leave on composition.

According to yet a further aspect, there is provided the use in a hair treatment composition of a particulate substance which is substantially unagglomerated or unaggregated, which has a modal primary particle size of 7–40 nm, and Youngs modulus of at least 4 GPa, preferably at least 6 GPa, for the purpose of bodifying or styling the hair.

The particulate substances are preferably used in the hair treatment compositions at a level of at least 0.05%, more preferably at least 0.1%. Conveniently the solids are present in the compositions at a level of 3% or less, more preferably 2% or less.

The Youngs modulus of particulates suitable for use according to the invention is at least 6 Gpa, and is preferably at least 10 Gpa. The modulus may conveniently be at least 30 Gpa, and is preferably in region 50–90 Gpa, though moduli up to 1,000 Gpa are contemplated, though the modulus is preferably less than about 500 GPa. Modulus may conveniently be measured by a variety of standard techniques available as ASTM protocols; for silicas, the modulus may conveniently be measured for the bulk material.

Conveniently, the particulate substance utilised in the compositions has a modal primary particle size in the region 7–25 nm, and prior to addition to the treatment composition is substantially unaggregated or unagglomerated. The composition is subsequently treated in such a way as to not deliberately coacervate the particulates Should some association between primary particles occur, it is preferable that the association is such that 50% or more, more preferably 75% or more, more preferably 90% or more, even more preferably 95% or more of the particles in the particulate substance have a particle size of less than 100 nanometers. When treated hair is observed, the primary particles deposit substantially as discreet particles, or as loosely associated monolayers of primary particles.

Conveniently the primary particles of the relatively hard, s substantially unaggregated and unagglomerated material are a silica.

Treatment compositions according to the invention which do comprise a silica preferably have the silica present in an unbound form, that is not retained in any form of polymer matrix, or otherwise involved in encapsulation. A degree of surface treating of the silica in some embodiments may however exist.

Conveniently the silica may be obtained as raw material in the form of a liquid material which is charge stabilised, in order to minimise agglomeration or aggregation of the raw material which might otherwise occur. Where the material is a silica, it can be positively or negatively surface charged.

Conveniently the discrete particles of the particulate substance are monodisperse, or narrowly polydisperse.

Compositions which are to be used for styling preferably contain no more than 3% of styling polymer, more preferably less than 1% of a styling polymer, preferably contain less than 0.1% by weight styling polymer, and are optimally free of styling polymer.

The hair styling polymers which are preferably absent from compositions according to the invention, or at least present in the low quantities referred to above are those which are capable of forming a film and holding the hair of the user in place after evaporation of the volatile components of the hair styling composition.

Such hair styling polymers are well known articles of commerce and many such polymers are available commercially which contain moieties which render the polymers cationic, anionic, amphoteric or nonionic in nature.

Examples of anionic hair styling polymers include copolymers of vinyl acetate and crotonic acid, terpolymers of vinyl acetate, crotonic acid and a vinyl ester of an alpha-branched saturated aliphatic monocarboxylic acid such as vinyl neodecanoate, copolymers of methyl vinyl ether and maleic anhydride (molar ratio about 1:1) wherein such copolymers are 50% esterified with a saturated alcohol containing from 1 to 4 carbon atoms such as ethanol or butanol, acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

Also present at similarly low levels if at all are amphoteric polymers which can contain cationic groups derived from monomers such as t-butyl aminoethyl methacrylate as well as carboxyl groups derived from monomers such as acrylic acid or methacrylic acid can also be used in the present invention.

Examples of nonionic hair styling polymers which are present at similarly low levels if at all are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and homopolymers of N-vinylpyrrolidone having an average molecular weight of about 1,000,000 sold under the name of PVP K-120. Other nonionic hair styling polymers similarly absent (or present at low levels) are cross-linked silicone resins or gums.

Examples of cationic hair styling polymers similarly ideally absent are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

In certain embodiments, compositions preferably contain a volatile silicone. If present, the volatile silicone is present at a level of at least 0.1% by weight of the composition. Preferably is present at a level of at least 0.5% by weight of the composition, but is preferably present at a level of no greater than 10% by weight of the composition. Preferably it is present at a level of 5% or less, more preferably at a level of 3% or less by weight of the composition.

Most surprisingly, the presence of a small amount of volatile silicone has been found to enhance the effect of the small particulate deposited.

The term "volatile" as used herein means that the material in question has a measurable vapour pressure.

The viscosity of the volatile silicone is generally less than 10 cst at 25° C. Viscosity can be measured by means of a glass capillary viscometer as set out further in Dow Corning Corporate Test Method CTM004 Jul. 20, 1970.

Preferred cyclic silicones are dimethyl siloxane cyclic tetramer (n=4) and dimethyl siloxane cyclic pentamer (n=5).

Preferred short chain linear silicones generally have viscosities of less than 5 cst at 25° C.

Silicones of the above described types are widely available, e.g. from Dow Corning as DC 244, 245, 344, 345 and 200 fluids, and Union Carbide as Silicone 7202 and 7158.

In a preferred embodiment, the small particulate used in compositions according to the invention is unaggregated unagglomerated amorphous silica. Silicas of this type tend to have a relatively low pore volume compared to other silicas, which in some circumstances may be an effectively zero pore volume, and also not produce the thickening effects often seen in aqueous solution with other types of gelled silica, such as hydrated silicas. A preferred source of the silica is Ludox TM40, Ludox HS-40 Ludox SM, or Ludox CL (anion stabilised), commercially available from Du Pont.

Conveniently, the silica is chosen to be one which is stable at the pH of the topical composition, or to have an optimised stability within e.g. 3, preferably within 2 pH units of the pH of the topical composition. Hence, in an alkaline composition such as e.g. a leave on mousse composition, a material such as e.g. Ludox TM40 (which is most stable at pH 9–10) may be preferred. However, for a topical composition such as a conditioner, which typically has a pH of 4.5–6.5, a silica which is stable at or around this pH is preferred. Suitable silicas for inclusion in such generally neutral or slightly acidic pH compositions (e.g. having a pH in the region 4.0–7.5) are preferably cationically charged silicas, such as e.g. Ludox CL. By "stable" in this context is meant that the topical composition shows no signs of flocculation after having been stored undisturbed at 25° C. for a period of 6 months.

Other suitable small particulates for use in compositions according to the invention include cross linked polymer particles, such as cross linked polystyrene which have a Youngs modulus within the boundaries, aluminas and alumina silicates of primary particle size 7–40 nm, and colloidal metals compositions such as colloidal titanium dioxide.

Without wishing to be bound by theory, it is thought that in compositions according to the invention the small, relatively hard particulates bind to the hair shaft during treatment with the treatment composition, and cause an increase in friction between the individual hair shafts. It is this increase in friction which is thought to account for the increase in body which is observed, and also the styling benefits. Users of the compositions also frequently report an increase in resistance to brushing in hair treated by the compositions. This may be accompanied by increased body in the hair, and also improved style retention.

However, the so-called "wet conditioning" properties of the hair are generally not adversely affected, and may even be improved. The amount of small particulate which is deposited is of the same order of magnitude to the amount deposited when larger silica particles are used, but the larger particle size silica has been found not to provide the dry combing benefits (in the form of styling and bodifying) that the smaller particles do, whilst also causing the treatment composition to have an undesirable relatively high wet combing force. Certainly in the leave on compositions examined a low wet combing force (equating to good wet conditioning) is desirable.

The benefits from use of compositions according to the invention may best be derived after the user has styled the hair. However the benefits may be derived whether the hair is dried by a hair dryer, or allowed to dry naturally.

Hair treatment compositions according to the invention may suitably take the form of shampoos, conditioners, sprays, mousses or lotions. Particularly preferred forms are shampoos, conditioners and mousses, including "3-in-1" styling shampoos, having cleaning, conditioning and styling properties.

A preferred hair treatment composition in accordance with the invention is a shampoo composition which, in addition to the silicone conditioning polymer comprises (further) surfactant to provide a deterging benefit. The deterging surfactant is selected from anionic, nonionic, amphoteric and zwitterionic surfactants, and mixtures thereof.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups. Other suitable nonionics include mono- or di-alkyl alkanolamides. Example include coco mono- or di-ethanolamide and coco mono-isopropanolamide.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

The surfactants are present in shampoo compositions of the invention in an amount of from 0.1 to 50% by weight, preferably from 0.5 to 30% by weight.

Hair treatment compositions in accordance with the invention may also take the form of hair conditioning compositions, which preferably comprise one or more cationic surfactants. The use of cationic surfactants is especially preferred, because these ingredients are capable of providing conditioning benefits to hair.

Examples of cationic surfactants include:
  quaternary ammonium hydroxides, e.g., tetramethylammonium hydroxide, alkyltrimethylammonium hydroxides wherein the alkyl group has from about 8 to 22 carbon atoms, for example octyltrimethylammonium hydroxide, dodecyltrimethyammonium hydroxide, hexadecyltrimethylammonium hydroxide, cetyltrimethylammonium hydroxide, octyldimethylbenzylammonium hydroxide, decyldimethylbenzylammonium hydroxide, stearyldi-methylbenzylammonium hydroxide, didodecyldimethylammonium hydroxide, dioctadecyldimethylammonium hydroxide, tallow trimethylammonium hydroxide, cocotrimethylammonium hydroxide, and the corresponding salts thereof, e.g., chlorides Cetylpyridinium hydroxide or salts thereof, e.g., chloride
  Quaternium -5
  Quaternium -31
  Quaternium -18
  and mixtures thereof.

In hair conditioning compositions according to the invention, the level of cationic surfactant is preferably from 0.01 to 10%, more preferably 0.05 to 5%, most preferably 0.1 to 2% by weight of the composition.

Hair treatment compositions of the invention may also is contain one or more additional conditioning agents, preferably selected from cationic polymers, protein hydrolyzates and quaternised protein hydrolysates.

Suitable cationic polymers include:
  Guar hydroxypropyltrimmonium chloride
  Poly(dimethyldiallyammonium chloride)
  Poly(dimethylbutenyl ammonium chloride) -a, w-bis (triethanolammonium chloride)
  Poly(dipropyldiallyammonium chloride)
  Poly(methyl-B-propaniodiallyammonium chloride)
  Poly(diallypiperidinium chloride)
  Poly(vinyl pyridinium chloride)
  Quaternised poly (vinyl alcohol)
  Quaternised poly (dimethylaminoethylmethacylate)
  Poly-Quaternium 7
  Poly-Quaternium 10
  Poly-Quaternium 11
  Poly-Quaternium 22
  Poly-Quaternium 16
  and mixtures thereof.

Suitable protein hydrolysates include lauryl dimonium hydroxy propylamino hydrolysed animal protein, available commercially under the trade name LAMEQUAT L, and hydrolysed keratin containing sulphur-bearing amino acids, available commercially under the trade name CROQUAT WKP.

An optional component of wash off compositions according to the invention is a non-volatile insoluble silicone. The silicone is insoluble in the aqueous matrix of the shampoo composition of the invention and so is present in an emulsified form, with the silicone present as dispersed particles.

Suitable silicones include polydiorganosiloxanes, in particular polydimethylsiloxanes which have the CTFA designation dimethicone.

Also suitable for use in compositions of the invention are hydroxyl functional silicones, in particular polydimethyl siloxanes having hydroxyl end groups which have the CTFA designation dimethiconol.

Also suitable for use in compositions of the invention are silicone gums having a slight degree of cross-linking, as are described for example in WO 96/31188. These materials can impart body, volume and stylability to hair, as well as good wet and dry conditioning.

A further preferred class of silicones for inclusion in shampoos of the invention are amino functional silicones. By "amino functional silicone" is meant a silicone containing at least one primary, secondary or tertiary amine group, or a quaternary ammonium group.

Examples of suitable amino functional silicones include:
  (i) polysiloxanes having the CTFA designation "amodimethicone", and the general formula:

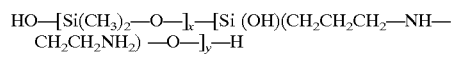

in which x and y are numbers depending on the molecular weight of the polymer, generally such that the molecular weight is between about 5,000 and 500,000.

(ii) polysiloxanes having the general formula:

in which:

G is selected from H, phenyl, OH or $C_{1-8}$ alkyl, e.g. methyl;

a is 0 or an integer from 1 to 3, preferably 0;

b is 0 or 1, preferably 1;

m and n are numbers such that (m+n) can range from 1 to 2000, preferably from 50 to 150;

m is a number from 1 to 2000, preferably from 1 to 10;

n is a number from 0 to 1999, preferably from 49 to 149, and

R' is a monovalent radical of formula $-C_qH_{2q}L$ in which q is a number from 2 to 8 and L is an aminofunctional group selected from the following:

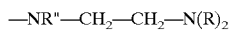

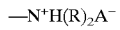

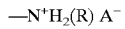

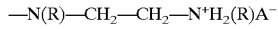

in which R" is selected from H, phenyl, benzyl, or a saturated monovalent hydrocarbon radical, e.g. $C_{1-20}$ alkyl, and A is a halide ion, e.g. chloride or bromide.

Suitable amino functional silicones corresponding to the above formula include those polysiloxanes termed "trimethylsilylamodimethicone" as depicted below, and which are sufficiently water insoluble so as to be useful in compositions of the invention:

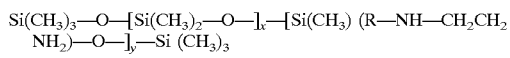

wherein x+y is a number from about 50 to about 500, and wherein R is an alkylene group having from 2 to 5 carbon atoms. Preferably, the number x+y is in the range of from about 100 to about 300.

(iii) quaternary silicone polymers having the general formula:

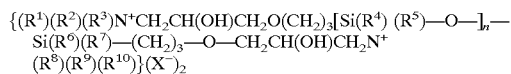

wherein $R^1$ and $R^{10}$ may be the same or different and may be independently selected from H, saturated or unsaturated long or short chain alk(en)yl, branched chain alk(en)yl and $C_5$–$C_8$ cyclic ring systems;

$R^2$ through $R^9$ may be the same or different and may be independently selected from H, straight or branched chain lower alk(en)yl, and $C_5$–$C_8$ cyclic ring systems;

n is a number within the range of about 60 to about 120, preferably about 80, and $X^-$ is preferably acetate, but may instead be for example halide, organic carboxylate, organic sulphonate or the like.

Suitable quaternary silicone polymers of this class are described in EP-A-0 530 974.

Amino functional silicones suitable for use in shampoos of the invention will typically have a mole % amine functionality in the range of from about 0.1 to about 8.0 mole %, preferably from about 0.1 to about 5.0 mole %, most preferably from about 0.1 to about 2.0 mole %. In general the amine concentration should not exceed about 8.0 mole % since we have found that too high an amine concentration can be detrimental to total silicone deposition and therefore conditioning performance.

Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones).

An example of a quaternary silicone polymer useful in the present invention is the material K3474, ex. Goldschmidt.

In general, the conditioning performance of the emulsified silicone in the shampoo composition of the invention tends to increase with increased viscosity of the silicone itself (not the emulsion or the final shampoo composition).

For dimethicone and dimethiconol-type silicones, the viscosity of the silicone itself is typically at least 10,000 cst, preferably at least 60,000 cst, most preferably at least 500,000 cst, ideally at least 1,000,000 cst. Preferably the viscosity does not exceed $10^9$ cst for ease of formulation. For amino functional-type silicones, the viscosity of the silicone itself is not particularly critical and can suitably range from about 100 to about 500,000 cst.

Emulsified silicones for use in hair shampoos of the invention will typically have an average silicone particle size in the composition of less than 30, preferably less than 20, more preferably less than 10 microns. In general, reducing the silicone particle size tends to improve conditioning performance. Most preferably the average silicone particle size of the emulsified silicone in the composition is less than 2 microns, ideally it ranges from 0.01 to 1 micron. Silicone emulsions having an average silicone particle size of ≦0.15 microns are generally termed microemulsions.

Particle size may be measured by means of a laser light scattering technique, using a 2600D Particle Sizer from Malvern Instruments.

Suitable silicone emulsions for use in the invention are also commercially available in a pre-emulsified form.

Examples of suitable pre-formed emulsions include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

Pre-formed emulsions of amino functional silicone are also available from suppliers of silicone oils such as Dow Corning and General Electric. Particularly suitable are emulsions of amino functional silicone oils with nonionic and/or cationic surfactant. Specific examples include DC929 Cationic Emulsion, DC939 Cationic Emulsion, DC949 cationic emulsion, and the nonionic emulsions DC2-7224, DC2-8467, DC2-8177 and DC2-8154 (all ex. Dow Corning).

Mixtures of any of the above types of silicone may also be used. Particularly preferred are hydroxyl functional silicones, amino functional silicones and mixtures thereof.

The total amount of silicone incorporated into compositions of the invention depends on the level of conditioning desired and the material used. A preferred amount is from 0.01 to about 10% by weight of the total composition although these limits are not absolute. The lower limit is determined by the minimum level to achieve conditioning and the upper limit by the maximum level to avoid making the hair and/or skin unacceptably greasy.

When the silicone is incorporated as a pre-formed emulsion as described above, the exact quantity of emulsion will of course depend on the concentration of the emulsion, and should be selected to give the desired quantity of silicone in the final composition.

A further optional component of hair treatment compositions of the invention is a deposition aid, preferably a cationic deposition polymer.

The cationic deposition aid will generally be present at levels of from 0.001 to 5%, preferably from about 0.01 to 1%, more preferably from about 0.02% to about 0.5% by weight. The polymer may be a homopolymer or be formed from two or more types of monomers. The molecular weight of the polymer will generally be between 5,000 and 10,000,000, typically at least 10,000 and preferably in the range 100,000 to about 2,000,000. The polymers will have cationic nitrogen containing groups such as quaternary ammonium or protonated amino groups, or a mixture thereof.

The cationic charge density has been found to need to be at least 0.1 meq/g, preferably above 0.8 or higher. The cationic charge density should not exceed 4 meq/g, it is preferably less than 3 and more preferably less than 2 meq/g. The charge density can be measured using the Kjeldahl method and should be within the above limits at the desired pH of use, which will in general be from about 3 to 9 and preferably between 4 and 8.

The cationic nitrogen-containing group will generally be present as a substituent on a fraction of the total monomer units of the cationic deposition polymer. Thus when the polymer is not a homopolymer it can contain spacer non-cationic monomer units. Such polymers are described in the CTFA Cosmetic Ingredient Directory, 3rd edition.

Suitable cationic deposition aids include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic deposition aids can comprise mixtures of monomer units derived from amine- and/or quaternary ammonium-substituted monomer and/or compatible spacer monomers.

Suitable cationic deposition aids include, for example: copolymers of 1-vinyl-2-pyrrolidine and 1-vinyl-3-methylimidazolium salt (e.g., Chloride salt) (referred to in the industry by the Cosmetic, Toiletry, and Fragrance Association, "CTFA". as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, N.J., USA) under the GAFQUAT tradename (e.g., GAFQUAT 755N); cationic diallyl quaternary ammonium-containing polymer including, for example, dimethyldiallyammonium chloride homopolymer and copolymers of acrylamide and dimethyldiallyammonium chloride, referred to in the industry (CTFA) as Polyquaternium 6 and Polyquaternium 7, respectively; mineral acid salts of amino-alkyl esters of homo-and co-polymers of unsaturated carboxylic acids having from 3 to 5 carbon atoms, as described in U.S. Pat. No. 4,009,256; and cationic polyacrylamides as described in our copending UK Application No. 9403156.4 (WO95/22311).

Other cationic deposition aids that can be used include polysaccharide polymers, such as cationic cellulose derivatives and cationic starch derivatives.

Cationic polysaccharide polymer materials suitable for use in compositions of the invention include those of the formula:

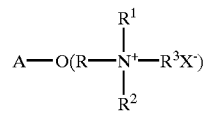

wherein: A is an anhydroglucose residual group, such as starch or cellulose anhydroglucose residual, R is an alkylene oxyalklene, polyoxyalkylene, or hydroxyalkylene group, or combination thereof, $R^1$, $R^2$ and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion as previously described.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g. as described in U.S. Pat. No. 3,962,418, incorporated by reference herein), and copolymers of etherified cellulose and starch (e.g., as described in U.S. Pat. No. 3,958,581, incorporated by reference herein).

As discussed above, the cationic deposition aid is water soluble. This does not mean, however, that it must be soluble in the hair treatment composition. Preferably, however, the polymer is either soluble in the composition, or in a complex coacervate phase in the composition, formed by the polymer and anionic material. Complex coacervates of the polymer can be formed with anionic surfactants or with anionic polymers that can optionally be added to the compositions of the invention (e.g., sodium polystyrene sulfonate).

Coacervate formation is dependent upon a variety of criteria such as molecular weight, concentration, and ratio of interacting ionic materials, ionic strength (including modification of ionic strength, for example, by addition of salts), charge density of the cationic and anionic species, pH, and temperature.

It is believed to be particularly advantageous for the cationic deposition aid to be present in the composition in a coacervate phase, or to form a coacervate phase upon application or rinsing of the composition to or from the hair. Complex coacervates are believed to more readily deposit on the hair. Thus, in general, it is preferred that the deposition aid exist in the composition as a coacervate phase or form a coacervate phase upon dilution. If not already a coacervate in the composition, the deposition aid will preferably exist in a complex coacervate form in the composition upon dilution with water to a water: composition weight ratio of about 20:1, more preferably at about 10:1, even more preferably at about 8:1.

Techniques for analysis of formation of complex coacervates are known in the art. For example, microscopic analyses of the compositions, at any chosen stage of dilution, can be utilised to identify whether a coacervate phase has formed. Such coacervate phase will be identifiable as an additional emulsified phase in the composition. The use of dyes can aid in distinguishing the coacervate phase from other insoluble phases dispersed in the composition.

Preferably the deposition aid is selected from the group comprising cationic polyacrylamides, hydroxyalkyl cellulose ethers and cationic guar derivatives. Particularly preferred deposition aids are Jaguar C13S with a cationic charge density of 0.8 meq/g. Jaguar C13S is guar hydroxypropyltriamonium chloride. Other particularly suitable materials include Jaguar C15, Jaguar C17 and Jaguar C16 and Jaguar C162. A preferred cellulose ether is Polymer JR400.

The composition may further comprise from 0.1 to 5% of a silicone suspending agent selected from selected from polyacrylic acids cross linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and Polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol (trade mark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Another ingredient that may advantageously be incorporated into hair treatment compositions of the invention is a fatty alcohol material. The use of such materials is especially preferred in conditioning compositions of the invention, in particular conditioning compositions which comprise one or more cationic surfactant materials. The combined use of fatty alcohol materials and cationic surfactants in conditioning compositions is believed to be especially advantageous, because this leads to the formation of a lamellar phase, wherein the cationic surfactant is dispersed.

Preferred fatty alcohols comprise from 8 to 22 carbon atoms, more preferably 16 to 20. Examples of preferred fatty alcohols are cetyl alcohol and stearyl alcohol. The use of these materials is also advantageous in that they contribute to the overall conditioning properties of compositions of the invention.

The level of fatty alcohol materials is conveniently from 0.01 to 10%, preferably from 0.1 to 5% by weight of the composition. The weight ratio of cationic surfactant to fatty alcohol is preferably from 10:1 to 1:10, more preferably from 4:1 to 1:8, most preferably from 1:1 to 1:4.

In particular when the composition according to the invention is a leave on composition, the hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin.

Carriers suitable for use with hair care compositions of the present invention include, for example, those used in the formulation of hair sprays, mousses, tonics, gels, oils, lotions, creams, pumpsprays, shampoos, conditioners, air infused styling foams and rinses. The choice of appropriate carrier will also depend on the particular copolymer (if any) to be used, and whether the product formulated is meant to be left on the surface to which it is applied, as well as how it is applied (e.g., hair spray, mousse, tonic, or gel), or rinsed off after use (e.g., shampoo, conditioner, rinse).

The carriers used herein can include a wide range of components conventionally used in hair care compositions. The carriers can contain a solvent to dissolve or disperse the particular copolymer being used, with water, the C1–C6 alcohols, lower alkyl acetate and mixtures thereof being preferred. The carriers can also contain a wide variety of additional materials such as acetone, hydrocarbons (such as isobutane, hexane, decene), halogenated hydrocarbons (such as Freons) and volatile silicon derivatives such as cyclomethicone. When the hair care composition is a hair spray, tonic, gel, air infused styling foams or mousse the preferred solvents include water, ethanol, volatile silicone derivatives, and mixtures thereof. The solvents used in such mixtures may be miscible or immiscible with each other.

Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane.

A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% of the composition. The level of propellant can be adjusted as desired but is generally from about 3% to about 30% of mousse compositions and from about 15% to about 50% of the aerosol hair spray compositions.

Suitable spray containers are well known in the art and include conventional, non-aerosol pump sprays i.e., "atomisers", aerosol containers or cans having propellant, as described above, and also pump aerosol containers utilising compressed air as the propellant.

Where the hair care compositions are conditioners and rinses the carrier can include a wide variety of conditioning materials. Where the hair care compositions are shampoos, the carrier can include, for example, surfactants, suspending agents, and thickeners.

The carrier can be in a wide variety of forms. For example, emulsion carriers, including oil-in-water, water-in-oil, water-in-oil-in-water, and oil-in-water-in-silicone emulsions, are useful herein. These emulsions can cover a broad range of viscosities, e.g., from about 100 cps to about 200,000 cps, measured at 25° C. These emulsions can also be delivered in the form of sprays using either mechanical pump containers or pressurised aerosol containers using conventional propellants. These carriers can also be delivered in the form of a mousse.

Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like).

Depending on the type of composition employed, one or more additional ingredients conventionally incorporated into hair treatment compositions may be included in compositions of the invention. Such additional ingredients include styling agents, such as resins and hair-setting polymers, perfumes, dyes, buffering or pH adjusting agents, viscosity modifiers, opacifiers, pearlescers, preservatives, antibacterial agents, antidandruff agents, foam boosters, proteins, moisturising agents, herb or other plant extracts and other natural ingredients.

The invention is further illustrated by way of the following non-limiting examples with reference to FIG. 1, which shows a graph of peak combing forces for conditioners containing various silicas.

EXAMPLE 1

A series of conditioners were assessed for friction modification of the hair. Conditioner A served as a control condition, whilst conditioner B is according to the invention. Conditioner C utilizes a silica which shows substantial degrees of aggregation and agglomeration (Aerosol 90), and is outside the scope of the invention.

|  | Conditioner A % w/w | Conditioner B % w/w | Conditioner C % w/w |
| --- | --- | --- | --- |
| Laurex CS (1) | 3.25 | 3.25 | 3.25 |
| Carsoquat 868 P (2) | 2.10 | 2.10 | 2.10 |
| Promulgen G (3) | 1.00 | 1.00 | 1.00 |
| Lexamine S13 (4) | 0.50 | 0.50 | 0.50 |
| Propylene glycol | 0.50 | 0.50 | 0.50 |
| Ludox TM-40 (40% active) | — | 3.75 | — |
| Aerosil 90 | — | — | 1.5 |
| Distilled water | To 100 | To 100 | To 100 |

(1) Cetostearyl alcohol
(2) Dicetyl dimethyl ammonium chloride
(3) Stearyl alcohol
(4) Lauryl amido propyl betaine 8 g, 25.4 cm hair switches were trimmed to 20.3 cm and washed in a surfactant base solution, and conditioned with conditioner products (A)–(C) above. In the method, 0.1 g of surfactant solution was applied per gram of hair, which was then washed for 30 seconds, rinsed for 30 seconds, washed for 30 seconds and rinsed for 1 minute.

Conditioner was then applied (0.1 g per gram of hair), washed in for 1 minute, and then rinsed out for 1 minute.

Whilst wet, the treated switch was de-tangled, enclosed within an environment chamber maintained at 20° C., 50% RH and attached to a load cell mounted in an Instron load frame. A comb is pulled mechanically through the switch a number of times, and the resulting time-force profile recorded. This process is repeated using 10 hair switches per product.

The wet switches were then dried for 1 hour in a drying cabinet maintained at 50° C. They are then placed in an environment chamber maintained at 20° C., 50% RH and allowed to equilibrate overnight. The dry switches are then tested the following day using the same methodology detailed above. The average peak combing force and associated standard error for both wet and dry experiments are then calculated from the recorded time-force profiles for each product.

To ensure silica deposition and fair comparison of the systems, silicon X-ray fluorescence spectroscopy was used to check silica deposition.

The results are shown below:

| Conditioner | Silica Deposition (ppm) |
| --- | --- |
| A | 5.2 ± 11.3 |
| B | 279.8 ± 15.3 |
| C | 400.2 ± 44.2 |

The peak dry and wet combing scores for conditioners (A)–(C) are shown graphically in FIG. 1.

In relation to the results and with reference to FIG. 1, conditioner (A) (control) demonstrates relatively low peak wet and dry combing force. In general, a low peak wet combing force is desirable, since it indicates a wet conditioning benefit to the user. Conversely, a high wet combing force is indicative to the user of poor conditioning qualities.

In relation to the invention, a relatively high peak dry combing force is desirable, since this is synonymous with high levels of style retention (in leave on compositions), and body.

As can be appreciated, the higher the peak dry combing force, the more effort is needed to drag a comb through the hair, which is synonymous to the user with hair body and style retention.

Of the compositions containing silica, composition (C) (containing Aerosil 90), although depositing higher actual amounts of silica, demonstrated a relatively high peak wet combing force (undesirable), and a relatively low peak dry combing force (indicative of relatively poor body/style retention). However, composition (B) according to the invention demonstrated improved conditioning (lower peak wet combing force) over the control conditioner, but substantially higher peak dry combing force, which is synonymous with body and style retention.

EXAMPLE 2

The following three mousse compositions were prepared, and dosed into a pressurized can;

| Example | A | B | C |
|---|---|---|---|
| Genamin KDMP (5) | 0.325 | 0.325 | 0.325 |
| Lorol C16 (6) | 0.32 | 0.32 | 0.32 |
| Lorol C18 (7) | 0.32 | 0.32 | 0.32 |
| CAPB (8) | 0.5 | 0.5 | 0.5 |
| DC245 (9) | 2.5 | 2.5 | 2.5 |
| Ludox TM-40 | 1.25 | 1.25 | 1.25 |
| DC1787 (10) | — | 1.2 | — |
| PVP K30 (11) | — | — | 0.1 |
| CAO3 BHT (12) | 0.02 | 0.02 | 0.02 |
| EDTA | 0.02 | 0.02 | 0.02 |
| Bronopol (13) | 0.01 | 0.01 | 0.01 |
| Perfume | 0.1 | 0.1 | 0.1 |
| CAP40 | 8 | 8 | 8 |
| Water | To 100 g | To 100 g | To 100 g |

(5) Behenyl trimethyl ammonium chloride
(6) C16 fatty alcohol
(7) C18 fatty alcohol
(8) Cocoamidopropyl betaine
(9) Volatile silicone
(10) Cross-linked non-volatile silicone emulsion, ex. Dow Corning
(11) Poly vinyl pyrollidone styling polymer
(12) Butyl hydroxy toluene (antioxidant)
(13) 2-bromo-2-nitropropane-1,3, diol (antimicrobial)

In the preparation, the Genamin KDMP, Lorol C16 and Lorol C18 were added to 20% of the total amount of water in the composition. The mixture was heated with vigorous stirring, and a blended phase formed at 80° C. in 15–20 minutes. The mixture was left to cool to room temperature.

In a separate mixing vessel the Ludox TM-40 was mixed with 30% of the total amount of water in the composition. In the case of Example 3, the PVP K30 was added as a 10% solution and stirred for 15 minutes. In all examples, the blended phase was then added with stirring, and the remaining water was added and mixed. The cocoamidopropyl betaine surfactant was then added, and mixed for 10 minutes, followed by the DC245 and minor components with further mixing for 15 minutes. The mixture was then canned and gassed with CAP 40.

The mousse formulation was then applied to mannequin heads and assessed.

To do this, the mannequin head is washed using a non-silicone based shampoo. The hair is towel dried, the test product is applied to either the right or left side of the head, and a control product is applied to the other half. The products are evenly distributed throughout the hair using the fingers, and the wet attributes assessed. The mannequin heads are then blow dried with a hair dryer and styled, and the dry attributes assessed. The style of the dried head was then assessed after one hour for volume and root lift changes.

The products were comparatively assessed against a control product (which always has a score of 5) on a 1–10 scale. A score greater than 5 indicates an improvement in that tribute on the control.

Results

| Selected attribute | Example A | Example B | Example C |
|---|---|---|---|
| Stickiness of hair | 7 | 7 | 6 |
| Stickiness of hands | 7 | 7 | 6 |
| Grip on brush | 6 | 7 | 7 |
| Ease of styling (style hold) | 5 | 5 | 5 |
| Root lift | 4 | 8 | 4 |
| Overall body | 6 | 6 | 7 |
| Natural feel | 5 | 6 | 6 |
| Natural movement | 4 | 6 | 4 |
| Stickiness of hair | 6 | 7 | 5 |

Example A (Ludox TM-40 in a conditioning base) results show an improvement in styling and body attribute scores suggesting that the Ludox TM-40 is frictionalising the hair due to the increase in grip in the absence of any polymer.

Example B (Ludox TM-40 in a conditioning base with cross-linked silicone) shows increases in root lift and other body attributes.

Example C (Ludox TM-40 in a conditioning base with 0.1% PVP K30) in this case a decrease in the stickiness scores is observed indicating that the formulation is becoming more sticky in the hands and in the hair. In addition, a decrease in the body attributes is observed.

EXAMPLE 3

The following compositions represent suitable topical compositions according to the invention:

Shampoo Compositions

| Ingredient | A | B | C | D |
|---|---|---|---|---|
| Ammonium lauryl sulphate | 12 | — | — | — |
| SLES | — | 14 | 12 | 4 |
| CAPB | 1 | 2 | 2 | 4 |
| Jaguar C13S (polymer) | 0.3 | 0.2 | 0.1 | 0 |
| Polymer JR 30 M | 0 | 0 | 0 | 0.3 |
| Ethylene glycol distearate | 2 | 1.5 | 1.5 | 0 |
| PDMS (1 McSt, 350 nm P.S.) | 1.5 | 0 | 3 | 0 |
| PDMS emulsion (60 KcSt, 35 nm P.S.) | 0 | 0 | 0 | 0.4 |
| Ludox TM 40 | 0.5 | 0.1 | 1 | 0.3 |
| Carbomer (Carbopol 940) | 0 | 0.2 | 0.2 | 0 |
| NaCl | 1 | 1 | 1.5 | 2 |
| Preservative | qs | qs | qs | QS |
| Fragrance | qs | qs | Qs | qs |
| Water | To 100 | To 100 | To 100 | To 100 |

Conditioner Compositions

| Ingredient | E | F | G | H |
|---|---|---|---|---|
| Cetyl trimethyl ammonium chloride | 0.7 | 1.1 | 0.7 | 0 |
| Cetostearyl alcohol | 3 | 4 | 2 | 4 |
| BTAC | 0 | 0 | 0 | 1.5 |
| Polysurf 67 (thickener | 0 | 0.05 | 0 | 0 |
| Natrasol 250 HHR (thickener) | 0 | 0 | 1 | 0 |
| PDMS (1 McSt visc., 350 nm P.S.) | 0 | 1 | 2 | 1 |
| DC 245 (Dow corning) | 1.2 | 0 | 0.5 | 0 |
| Stearyl stearate | 0.5 | 0 | 0 | 0.5 |
| Paraffin wax | 0 | 0 | 0 | 2 |
| Ludox TM40 | 0.5 | 0.1 | 2 | 1 |
| Preservative | Qs | Qs | Qs | Qs |
| Fragrance | Qs | Qs | Qs | Qs |
| Water | To 100 | To 100 | To 100 | To 100 |

EXAMPLE 4

Conditioner A formulation as used in Example 1 above was used at different levels of silica, with and without the presence of volatile silicone, to determine the level of deposition of silica on hair. The protocol for determining deposition was the same as that outlined in Example 1 above. The results are shown below:

| Ludox TM40 (% wt) | DC 245 (% wt) | Silica deposited (ppm) | Error (ppm) |
|---|---|---|---|
| 0.5 | 0 | 207 | 58 |
| 1.0 | 0 | 343 | 78 |
| 1.5 | 0 | 338 | 47 |
| 0.5 | 1.8 | 531 | 91 |
| 1.0 | 1.8 | 665 | 125 |
| 1.5 | 1.8 | 947 | 108 |

What is claimed is:

1. A hair treatment composition which comprises 0.01–5.0 wt % of a particulate substance which is substantially unagglomerated or unaggregated prior to incorporation in the composition, which particulate substance has a modal primary particle size of 7–40 nm, and a Youngs modulus of at least 4 GPa.

2. A hair treatment composition according to claim 1, wherein the particulate substance has a Youngs modulus of at least 6 Gpa.

3. A hair treatment composition according to claim 1 or claim 2, wherein the composition is a wash off composition which is a shampoo or conditioner composition.

4. A hair treatment composition according to claim 1 or claim 2, wherein composition is a leave on composition which is a gel, mousse, cream, lotion, air infused styling foam or spray composition.

5. A hair treatment composition according to claim 3, wherein the composition contains a volatile silicone.

6. A hair treatment composition according to claim 5, wherein the volatile silicone is present at a level of 0.1–5 wt % of the composition.

7. A hair treatment composition according to claim 1, wherein the composition contains at least 0.05 wt. % of the particulate substance.

8. A hair treatment composition according to claim 1, wherein the composition contains less than 3 wt. % of the particulate substance.

9. A hair treatment composition according to claim 1, wherein the particulate substance has a Youngs modulus of at least 10 GPa.

10. A hair treatment composition according to any of the preceding claims, wherein the particulate has a modal particle size of 7–25 nm.

11. A hair treatment composition according to claim 1, wherein the association between the primary particles in the composition is such that at least 75% of the particles of particulate in the composition are in the form of monodisperse primary particles or have an associated particle size of less than 100 nm.

12. A hair treatment composition according to claim 1, wherein the particular substance is substantially un aggregated and unagglomerated silica.

13. A hair treatment substance according to claim 12, wherein the substantially unaggregated and unagglomerated silica is either positively of negatively surface charged.

14. A hair treatment composition according to claim 1, wherein the particulate substance is titanium dioxide.

15. A hair treatment composition according to claim 1, wherein the composition contains less than 3 wt. % of a styling polymer.

16. A method of treating hair comprising applying thereto a hair treatment composition which comprises 0.01–5.0 wt % of a particulate substance which is substantially unagglomerated or unaggregated, which has a modal primary particle size of 7–40 nm, and a Youngs modulus of at least 4 GPa, and subsequently styling the hair.

17. A method for bodifying or styling hair which comprises contacting said hair with a composition in accordance with claim 1.

18. A hair treatment composition according to claim 7, wherein the composition contains at least 0.1% by wt. of the particulate substance.

19. A composition in accordance with claim 8, wherein the composition contains less than 2 wt. % of the particulate substance.

20. A composition in accordance with claim 9, wherein the particulate substance has a Youngs modulus of at least 30 GPa.

21. A hair treatment composition in accordance to claim 20, wherein the particulate substance has a Youngs modulus of about 50–90 GPa.

22. A composition in accordance with claim 11, wherein the association between the primary particles in the compositions is such that at least 95% of the particles of particulate in the composition are in the form of monodispersed primary particles or have associated particle size of the less than 100 nm.

23. A composition in accordance with claim 15, wherein the composition is free of styling polymer.

* * * * *